(12) United States Patent
Feldman et al.

(10) Patent No.: US 12,239,417 B2
(45) Date of Patent: Mar. 4, 2025

(54) OPTOACOUSTIC PROBE

(71) Applicant: Seno Medical Instruments, Inc., San Antonio, TX (US)

(72) Inventors: Samuel Henry Feldman, San Antonio, TX (US); Xavier Saenz, San Antonio, TX (US); Jeffrey Nelson Harris, San Antonio, TX (US); George Lamberson, San Antonio, TX (US)

(73) Assignee: SENO MEDICAL INSTRUMENTS, INC., San Antonio, TX (US)

( * ) Notice: Subject to any disclaimer, the term of this patent is extended or adjusted under 35 U.S.C. 154(b) by 526 days.

(21) Appl. No.: 17/387,743

(22) Filed: Jul. 28, 2021

(65) Prior Publication Data

US 2023/0033766 A1 Feb. 2, 2023

(51) Int. Cl.
| | |
|---|---|
| *A61B 5/00* | (2006.01) |
| *G02B 26/00* | (2006.01) |
| *G02B 26/08* | (2006.01) |
| *G02F 1/29* | (2006.01) |

(52) U.S. Cl.
CPC .......... *A61B 5/0095* (2013.01); *A61B 5/7221* (2013.01); *G02B 26/004* (2013.01); *G02B 26/0875* (2013.01); *G02F 1/29* (2013.01); *G02F 2203/12* (2013.01)

(58) Field of Classification Search
CPC .................................................. A61B 5/0095
See application file for complete search history.

(56) References Cited

U.S. PATENT DOCUMENTS

| | | | | |
|---|---|---|---|---|
| 2011/0188251 | A1* | 8/2011 | Kalms | A61B 5/0095 82/1.11 |
| 2015/0094599 | A1* | 4/2015 | Kim | G02B 3/14 359/666 |
| 2015/0126858 | A1* | 5/2015 | Choi | A61B 1/00172 600/478 |
| 2015/0148652 | A1* | 5/2015 | Wanda | A61B 5/14542 600/407 |
| 2016/0051149 | A1* | 2/2016 | Viator | A61B 5/445 600/407 |
| 2018/0011061 | A1* | 1/2018 | Furukawa | A61B 5/0091 |

\* cited by examiner

*Primary Examiner* — Joseph M Santos Rodriguez
(74) *Attorney, Agent, or Firm* — The Small Patent Law Group LLC; Josef L. Hoffmann

(57) ABSTRACT

An optoacoustic probe for optoacoustic imaging of a volume is provided that includes a housing extending from a distal end operable to contact the volume to a proximal end. The optoacoustic probe includes a light source configured to generate light that is transmitted along a light pathway to generate return signals when the light reacts with the volume, and a transducer assembly including a transducer configured to receive the optoacoustic return signals and an acoustic lens provided over the transducer. The optoacoustic probe also includes a steering assembly coupled within the housing and configured to steer the light pathway to generate the light along the light pathway at different scanning areas of the volume based on the return signals.

12 Claims, 8 Drawing Sheets

OPTOACOUSTIC PROBE

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

TECHNICAL FIELD

The present invention relates in general to the field of medical imaging, and in particular to a system relating to optoacoustic imaging.

BACKGROUND

Optoacoustic imaging systems visualize thin tissue slices noninvasively through skin at a tissue site. A tissue site may contain a variety of tissue structures that may include, for example, tumors, blood vessels, tissue layers, and components of blood. In optoacoustic imaging systems, light is used to deliver optical energy to a planer slice of the tissue site, which as a result of optical absorption with the tissue structures, produce acoustic waves. An image spatially representing the tissue site can be generated by performing image reconstruction on acoustic signals that return to an ultrasound transducer array. Because biological tissue scatters impinging optical energy in many directions the optical energy can be absorbed by tissue structures outside of a targeted region, which can generate acoustic return signals that interferes with the imaging of tissue structures within the targeted region.

In addition, often times difficulties can occur as a result of the transducer sensing artifacts, that are not representative of the biological tissue. These artifacts can result in inaccurate results and difficulties in diagnosis. In particular, there is no manner for the clinician to differentiate between an artifact and an irregularity. In addition, different patients have different skin types, and irregularities such as tumors, lumps, masses, or the like, are located at different depths in the skin. As a result of the differing skin types, obtaining desired imaging depth can create difficulties. Still, there is no manner in which to account for these types of issues.

BRIEF SUMMARY

New and useful systems, apparatuses, and methods for providing optoacoustic imaging are set forth in the appended claims. Illustrative embodiments are also provided to enable a person skilled in the art to make use the claimed subject matter.

Objectives, advantages, and a preferred mode of making and using the claimed subject matter may be understood best by reference to the accompanying drawings in conjunction with the following detailed description of illustrative embodiments.

In accordance with embodiments herein, an optoacoustic probe for optoacoustic imaging of a volume is provided that includes a housing extending from a distal end operable to contact the volume to a proximal end. The optoacoustic probe also includes a light source within the housing and configured to generate light that is transmitted along a light pathway to generate return signals when the light reacts with the volume, and a transducer assembly including a transducer configured to receive the optoacoustic return signals and an acoustic lens provided over the transducer. The optoacoustic probe also includes a steering assembly coupled within the housing and configured to steer the light pathway to generate the light along the light pathway at different scanning areas of the volume, and a microcontroller including one or more processors, and a memory coupled to the one or more processors. The memory stores program instructions, wherein the program instructions are executable by the one or more processors to obtain the return signals generated from the light pathway reflecting from the volume, and steer the light pathway with the steering assembly based on the return signals.

Optionally, the steering assembly comprises a spatial light modulator (SLM) coupled to the light source and configured to deflect the light pathway. In one aspect, the SLM is a phase only one-dimensional phase modulator formed of a liquid crystal material. Alternatively, the steering assembly includes an optical window configured to transmit the light along the light pathway to the volume, and an actuator coupled to the optical window to move the optical window from a first angle to a second angle. In one aspect, the optical window is cylindrical, and the actuator is configured to rotate the optical window from a first position to a second position to steer the light pathway. Alternatively, the steering assembly comprises a deformable lens having a radius of curvature configured to vary to steer the light pathway. In one aspect, the steering assembly further comprises a piston pump coupled to the deformable lens to vary hydraulic fluid within the deformable lens to vary the radius of curvature. In another alternative embodiment, the steering assembly comprises a synthetic material coupled to an actuator to steer the light pathway.

Optionally, the one or more processors of the microcontroller are further configured to identify a candidate irregularity based on the return signals, determine a location of the candidate irregularity, and steer the light pathway toward the candidate irregularity. In one aspect, the one or more processors of the microcontroller are further configured to verify that the candidate irregularity is not an artifact based on steering the light pathway toward the candidate irregularity. In another aspect, the one or more processors of the microcontroller are further configured to determine skin density of a patient based on the return signals, and steer the light pathway based on the skin density determined.

In one or more embodiments, a computer implemented method for optoacoustic imaging with an optoacoustic probe is provided. Under control of one or more processors configured with specific executable instructions, the method includes obtaining return signals by directing a light pathway to a location in a scanning area of a volume, and obtaining optoacoustic imaging data based on the return signals. The method also includes determining a location of a candidate irregularity based on the optoacoustic imaging data, and steering the light pathway toward the candidate irregularity to determine whether the candidate irregularity is an irregularity.

Optionally, determining whether the candidate irregularity is an irregularity includes verifying that the candidate irregularity is not an artifact based on steering the light pathway toward the candidate irregularity. In one aspect, steering the light pathway toward the candidate irregularity includes deflecting the light pathway utilizing a spatial light modulator (SLM) coupled to a light source. In another aspect, steering the light pathway toward the candidate irregularity includes rotating an optical window of the probe from a first angle to a second angle with an actuator coupled to the optical window. Alternatively, steering the light pathway toward the candidate irregularity includes varying hydraulic fluid within a deformable lens of the probe with a piston pump to vary a radius of curvature of the deformable lens.

In one or more embodiments, a computer implemented method for optoacoustic imaging with an optoacoustic probe is provided. Under control of one or more processors configured with specific executable instructions, the method includes obtaining return signals by directing a light pathway to a location in a scanning area of a volume, and obtaining optoacoustic imaging data based on the return signals. The method can also include determining skin density of the patient based on the optoacoustic imaging data, and steering the light pathway based on the skin density determined.

Optionally, steering the light pathway toward the candidate irregularity includes deflecting the light pathway utilizing a spatial light modulator (SLM) coupled to a light source. Alternatively, steering the light pathway toward the candidate irregularity includes rotating an optical window of the probe from a first angle to a second angle with an actuator coupled to the optical window. In yet another example, steering the light pathway toward the candidate irregularity includes varying hydraulic fluid within a deformable lens of the probe with a piston pump to vary a radius of curvature of the deformable lens.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

Figure 1:
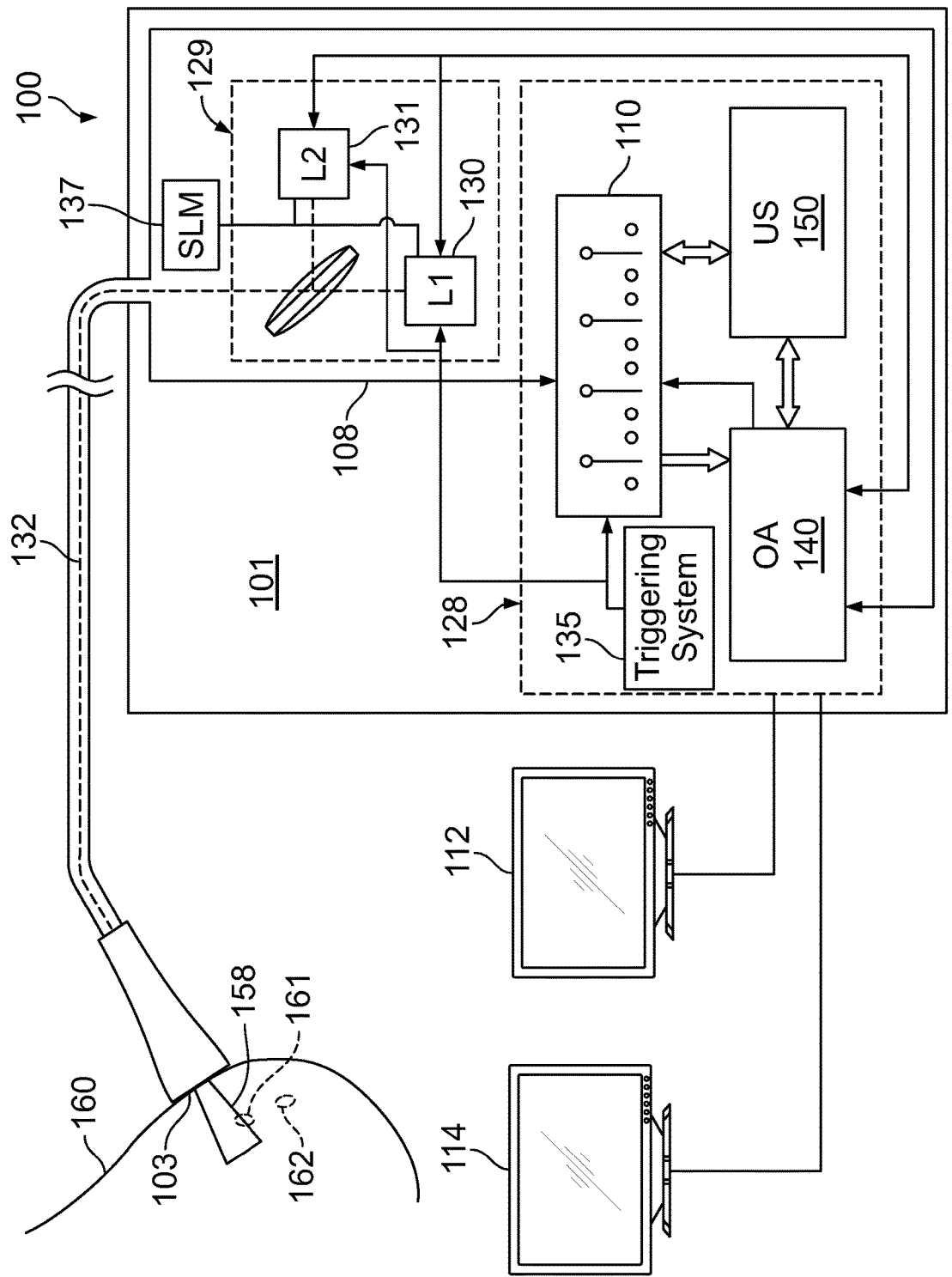
FIG. 1 shows a schematic block diagram illustrating an embodiment of an optoacoustic system that may be used as a platform for the methods and devices disclosed herein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments, but not other embodiments.

The systems and methods are described below with reference to, among other things, block diagrams, operational illustrations and algorithms of methods and devices to provide optoacoustic imaging with out-of-plane artifact suppression. It is understood that each block of the block diagrams, operational illustrations and algorithms and combinations of blocks in the block diagrams, operational illustrations and algorithms, can be implemented by means of analog or digital hardware and computer program instructions.

These computer program instructions can be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some cases, frequency domain-based algorithms require zero or symmetric padding for performance. This padding is not essential to describe the embodiment of the algorithm, so it is sometimes omitted from the description of the processing steps. In some cases, where padded is disclosed in the steps, the algorithm may still be carried out without the padding. In some cases, padding is essential, however, and cannot be removed without corrupting the data.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying figures. As will be apparent to one of skill in the art, the data structures and processing steps described herein may be implemented in a variety of other ways without departing from the spirit of the disclosure and scope of the invention herein and should not be construed as being limited to the embodiments set forth herein. Rather, these embodiments are provided so that this disclosure will be thorough and complete, and will fully convey the concept of the disclosure to those skilled in the art.

Embodiments herein may be implemented in connection with one or more of the systems and methods described in one or more of the following patents, publications and/or published applications, all of which are expressly incorporated herein by reference in their entireties:

U.S. Pat. No. 7,999,161, titled "Laser-Activated Nanothermolysis Of Cells" filed Jul. 23, 2007;

U.S. Pat. No. 9,289,191, titled "System and method for Acquiring Optoacoustic Data and Producing Parametric Maps Thereof", and filed Jun. 13, 2012;

U.S. Pat. No. 9,517,055, titled "System And Method For Acquiring Optoacoustic Data And Producing Parametric Maps Using Subband Acoustic Compensation" filed Nov. 25, 2013;

U.S. Pat. No. 9,724,072, titled "System And Method For Mixed Modality Acoustic Sampling" filed Dec. 13, 2013;

U.S. Pat. No. 9,456,805, titled "System And Method For Acquiring Optoacoustic Data And Producing Parametric Maps Using Interframe Persistent Artifact Removal" filed Dec. 19, 2013;

U.S. Publication 2016/0199037, titled "System And Method For Acquiring Optoacoustic Data And Producing Parametric Maps thereof" filed Mar. 22, 2016;

U.S. Publication 2017/0035388, titled "System And Method For Mixed Modality Acoustic Sampling" filed Oct. 18, 2016;

U.S. Pat. No. 9,792,686, titled "System And Method For Acquiring Optoacoustic Data And Producing Parametric Maps Using Subband Acoustic Compensation" filed Nov. 17, 2016;

U.S. Publication 2017/0296151, titled "System And Method For Mixed Modality Acoustic Sampling" filed Jun. 30, 2017;

U.S. Publication 2013/0109950, titled "Handheld Optoacoustic Probe" filed Nov. 2, 2011;

U.S. Publication 2016/0296121, titled "Handheld Optoacoustic Probe" filed May 2, 2016;

U.S. Pat. No. 8,686,335, titled "System And Method For Adjusting The Light Output Of An Optoacoustic Imaging System" filed Dec. 31, 2011;

U.S. Pat. No. 9,528,936, titled "System And Method For Adjusting The Light Output Of An Optoacoustic Imaging System" filed Mar. 31, 2014;

U.S. Publication 2017/0108429, titled "System And Method For Adjusting The Light Output Of An Optoacoustic Imaging System" filed Dec. 27, 2016;

U.S. Pat. No. 9,330,452, titled "Statistical Mapping In An Optoacoustic Imaging System" filed Mar. 11, 2013;

U.S. Pat. No. 9,836,838, titled "Statistical Mapping In An Optoacoustic Imaging System" filed May 3, 2016;

U.S. Publication 2018/0061050, titled "Statistical Mapping In An Optoacoustic Imaging System" filed Nov. 6, 2017;

U.S. Pat. No. 9,610,043, titled "System And Method For Producing Parametric Maps Of Optoacoustic Data" filed Jun. 13, 2012;

U.S. Publication 2017/0100040, titled "System And Method For Producing Parametric Maps Of Optoacoustic Data" filed Dec. 21, 2016;

U.S. Publication 2013/0338501, titled "System And Method For Storing Data Associated With The Operation Of A Dual Modality Optoacoustic/Ultrasound System" filed Jun. 13, 2012;

U.S. Publication 2013/0338475, titled "Optoacoustic Imaging System With Fiber Optic Cable" filed Jun. 13, 2012;

U.S. Publication 2014/0194723, titled "Multi-Layer Coating For Optoacoustic Probe" filed Jan. 13, 2014;

U.S. Publication 2017/0150890, titled "Optoacoustic Probe With Multi-Layer Coating" filed Jan. 31, 2017;

U.S. Pat. No. 9,615,750, titled "Methods And Compositions For Carrier Agents And Clearing Agents Used In Optoacoustic Imaging Systems" filed Jun. 14, 2012;

U.S. Publication 2013/0116538, titled "Optoacoustic Imaging Systems And Methods With Enhanced Safety" filed Oct. 19, 2012;

U.S. Publication 2015/0297090, titled "Optoacoustic Imaging Systems And Methods With Enhanced Safety" filed Jan. 23, 2015;

U.S. Publication 2013/0289381, titled "Dual Modality Imaging System For Coregistered Functional And Anatomical Mapping" filed Nov. 2, 2012;

U.S. Pat. No. 9,757,092, titled "Method For Dual Modality Optoacoustic Imaging" filed Nov. 2, 2012;

U.S. Publication 2014/0039293, titled "Optoacoustic Imaging System Having Handheld Probe Utilizing Optically Reflective Material" filed Jan. 22, 2013;

U.S. Publication 2017/0014101, titled "Dual Modality Imaging System For Coregistered Functional And Anatomical Mapping" filed Sep. 27, 2016;

U.S. Publication 2013/0303875, titled "System And Method For Dynamically Varying The Angle Of Light Transmission In An Optoacoustic Imaging System" filed Nov. 2, 2012;

U.S. Pat. No. 9,445,785, titled "System And Method For Normalizing Range In An Optoacoustic Imaging System" filed Dec. 21, 2012;

U.S. Pat. No. 9,282,899, titled "System And Method For Detecting Anomalous Channel In An Optoacoustic Imaging System" filed Dec. 21, 2012;

U.S. Publication 2014/0005544, titled "System And Method For Providing Selective Channel Sensitivity In An Optoacoustic Imaging System" filed Dec. 21, 2012;

U.S. Publication 2016/0317034, titled "System And Method For Providing Selective Channel Sensitivity In An Optoacoustic Imaging System" filed Jul. 11, 2016;

U.S. Pat. No. 9,445,786, titled "Interframe Energy Normalization In An Optoacoustic Imaging System" filed Jan. 22, 2013;

U.S. Publication 2017/0000354, titled "Interframe Energy Normalization In An Optoacoustic Imaging System" filed Sep. 19, 2016;

U.S. Publication 2014/0206978, titled "Probe With Optoacoustic Isolator" filed Jan. 22, 2013;

U.S. Pat. No. 9,743,839, titled "Playback Mode In An Optoacoustic Imaging System" filed Mar. 15, 2013;

U.S. Publication 2017/0332916, titled "Playback Mode In An Optoacoustic Imaging System" filed Jul. 27, 2017;

U.S. Pat. No. 9,398,893, titled "System And Method For Diagnostic Vector Classification Support" filed Mar. 11, 2014;

U.S. Pat. No. 10,026,170, titled "System And Method For Diagnostic Vector Classification Support" filed Jul. 19, 2016

U.S. application Ser. No. 16/022,138, titled "System And Method For Diagnostic Vector Classification Support" filed Jun. 28, 2018;

U.S. Pat. No. 9,730,587, titled "Diagnostic Simulator" filed Mar. 15, 2013;

U.S. Publication 2017/0332915, titled "Diagnostic Simulator" filed Jul. 27, 2017;

U.S. Pat. No. 8,823,928, titled "Light Output Calibration In An Optoacoustic System" filed Mar. 15, 2013;

U.S. Pat. No. 9,163,980, titled "Light Output Calibration In An Optoacoustic System" filed Jul. 11, 2014;

U.S. Pat. No. 9,814,394, titled "Noise Suppression In An Optoacoustic System" filed Mar. 15, 2013;

U.S. Publication 2018/0078144, titled "Noise Suppression In An Optoacoustic System" filed Nov. 13, 2017;

U.S. Pat. No. 9,733,119, titled "Optoacoustic Component Utilization Tracking" filed Mar. 15, 2013;

U.S. Publication 2017/0322071, titled "Optoacoustic Component Utilization Tracking" filed Jul. 27, 2017;

U.S. Publication 2015/0101411, titled "Systems And Methods For Component Separation In Medical Imaging" filed Oct. 13, 2014;

U.S. Publication 2015/0305628, titled "Probe Adapted To Control Blood Flow Through Vessels During Imaging And Method Of Use Of Same" filed Feb. 27, 2015.

U.S. Publication 2016/0187481, titled "Opto-Acoustic Imaging System With Detection Of Relative Orientation Of Light Source And Acoustic Receiver Using Acoustic Waves" filed Oct. 30, 2015.

As used herein, the term "steering assembly" refers to any and all combinations of mechanisms, devices, parts, structures, systems, or the like that can move a light pathway generated by a light source of a probe without movement of the probe. The steering assembly can include mechanical systems, electrical systems, hydraulic systems, pneumatic systems, etc. In one example, the steering assembly can include a spatial light modulator (SLM) that is coupled to a light source and varies the light pathway through phase modulation of the light of the light source. In another example the steering assembly can include an optical window and an actuator that rotates the window to varying positions. In another example, the steering assembly can include a deformable lens and a piston pump that varies hydraulic fluid in the deformable lens to change a radius of curvature of the lens. In yet another example, the steering assembly may include a synthetic material used with an actuator to move the light pathway.

As used herein, the term "scanning area" refers to any and all areas and partial volumes of a volume that a light pathway transmits onto. The scanning area can include locations or targets of animal and human tissues and organs such as, for example, breast tissue. A scanning area may contain a variety of different structures that may include, for example, tumors, blood vessels, tissue layers, and components of blood. The scanning area is the area where return signals are generated as a result of the light of the light pathway interacting with the volume being examined.

As used herein, the term "candidate irregularity" refers to any and all potential masses, cells, lumps, tumors, shapes, sizes, artifacts, etc. detected in an image generated by a probe based on return signals. The candidate irregularity includes all irregularities including masses, cells, lumps, tumors, etc. detected and imaged by a probe, and all false irregularities, artifacts, etc. also detected and imaged by the probe.

As used herein the terms "steer" and "steering" refers to any and all movement, change, deflection, diffraction, angling, varying, etc. of the light of the light pathway by a steering assembly. Steering may be accomplished electrically, magnetically, mechanically, haptically, hydraulically, pneumatically, or the like. The result of steering is a changing of the scanning area of the probe based on a steering assembly and not based on movement of the probe by a clinician. While steering can occur while the clinician is moving the probe, the steering is not dependent on the clinician to occur.

Provided are probes and methods for moving light along a light pathway during imaging. In particular, instead of providing a light pathway that simply exits an optical window and is moved as the probe itself moves, mechanical, electrical, optical, etc. devices, components, systems, etc. are provided to allow movement of the light of the light pathway without the need of the physician to move the probe. As a result, the light pathway can be moved upwards, downwards, left, and right without movement of the probe. This allows functionality including the ability to determine if a detection is the result of an artifact or irregularity in a volume by refocusing the light on the area where the artifact/irregularity is detected. In addition, navigation into the volume is facilitated by also moving the light pathway, allowing for adjustments to the skin properties of the patient, resulting in deeper penetration of the light pathway for viewing. Movement of the light pathway may be provided manually by a clinician, or as a result of feedback obtained by the probe.

Turning to FIG. 1, generally, device 100 provides an optoacoustic system. In an embodiment, the device 100 includes a probe 102 connected via a light pathway 132 and an electrical path 108 to a system chassis 101. One or more displays 112, 114, which may be touch screen displays, are provided for displaying images and all or portions of the device 100 user interface. One or more other user input devices (not shown) such as a keyboard, mouse, and various other input devices (e.g., dials and switches) may be provided for receiving input from an operator.

Within the system chassis 101 is housed a light subsystem 129 and a computing subsystem 128. The computing subsystem 128 includes one or more computing components for optoacoustic control and analysis; these components may be separate, or integrated. In an embodiment, the computing subsystem comprises a relay system 110, a triggering system 135, an optoacoustic processing and overlay system 140 and an ultrasound instrument 150. In one embodiment, the triggering system 135 is configured to actuate and control operation of the light sources 130, 131.

The light sources 130, 131 in one example are lasers that each emit a determined wavelength of light. The light sources 130, 131 are configured to generate the light in order to form the light pathway 132. The light sources 130, 131 are consequently utilized in generating return signals for imaging purposes by generating the light for the light pathway 132 that is located at a scanning area 158 of a volume 160.

In one example, a steering assembly 163 is provided that includes at least one of light sources 130, 131 and a spatial light modulator (SLM) 137. The SLM 137 can be provided to vary, or adjust and light pathway 132. In one example, the SLM 137 is a phase only one-dimensional phase modulator, and can be formed of a liquid crystal material that deflects a beam of light to provide diffraction. By controlling the diffraction, the angle of the light pathway 132 may be varied to move the light pathway 132 internally within the chassis 101 without movement of an optical window, utilizing a deformable lens, utilizing an optical device later in the light pathway 132, etc. In one embodiment, the SLM 137 can include numerous phase-synchronized microwave sources operating with a time delay to alter the phase of the light beam generated by a light source 130 or 131, and provide a new array to steer the light pathway 132 to a different scanning area 158 of the volume 160. The new array is focused on a different location of the volume 160 than the previous array before the phase of the light pathway 132 is altered.

The volume 160 can include organic tissue, phantom, or other volume 160 that may have one or more irregularities, or inhomogeneities, 161, 162, such as e.g., a tumor, within. An ultrasound gel (not shown) or other material may be used to improve acoustic coupling between the probe 102 and the surface of the volume 160 and/or to improve optical energy transfer. In use, the probe 102 may be moved by a physician against the volume to locate and identify the irregularities 161, 162. After the probe is initial located, the light pathway 132 that may be varied, or moved, including in one example by the SLM 137 to locate the light pathway 132 toward an irregularity to verify the irregularity is not an artifact, to account for the skin density of the volume at the location, or the like.

Figure 2:
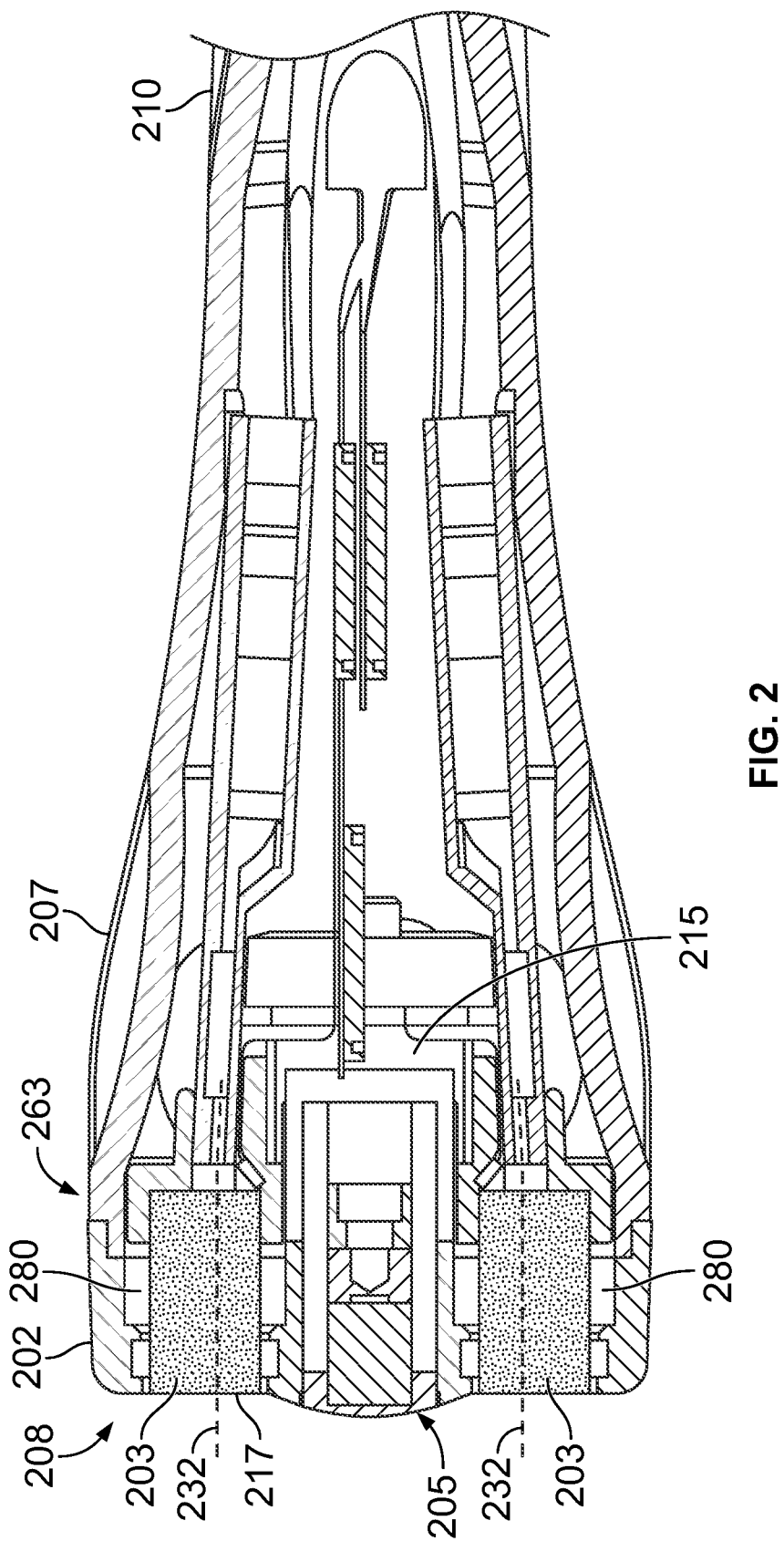
FIG. 2 shows a sectional view of an embodiment of a probe that may be used in connection with the methods and other devices disclosed herein.

Turning now to FIG. 2, another example probe 202 is provided that is configured to vary a light pathway 232 with a steering assembly 263 once the probe is placed against a volume in order to detect irregularities. FIG. 2 illustrates an orthogonal view to show the interior of an example probe 202. As illustrated, the probe 202 includes a housing 207 that extends from a distal end 208 to a proximal end 210 and includes an ultrasound transducer 215 covered by an acoustic lens 205. To this end, the housing 207 extends from the distal end 208 operable to contact the volume to the proximal end 210 that can be gripped by a clinician. The housing 207 may be made of any material, and can be of size and shape such that a clinician can move the probe 202 relative to a volume. The probe 202 of FIG. 2 also can include a probe face 217 at the distal end 208 of the housing 207. The probe 202 also includes one or more optical windows 203 through which the light transmitted along light pathway 232 can be transmitted to the surface of a volume, for example, a three-dimensional volume.

The term "optical window," as used here, is not limited to an element having a particular structural, mechanical, or optical characteristic. Instead, the term is used to refer to an element that may or may not affect light passing therethrough, but will permit at least a substantial portion of the light incident on a surface of the optical window that is adjacent, or at least substantially proximate to the light pathway 232 to exit the probe 202 in a manner that is dependent on the properties of the optical window 203. In an embodiment, the optical window 203 is transparent or substantially transparent, permitting transmission of light, specifically, light emitted from the end of the light path 232, to the volume when the distal end of the housing 207 contacts the volume.

In one example, a steering assembly 263 is provided that includes the optical window 203. Optionally, the optical window 203 is generally cylindrical and is coupled to an actuator 280 of the steering assembly 263 such as a motor that rotates the window. In this manner, the actuator 280 is able to move, or steer the light pathway 232 as the light pathway 232 is transmitted through the optical window 203 to numerous different position on the volume, including from a first position to a second position. The actuator 280 in example embodiments can move the lens upward, downward, side to side, rotate the optical window, pivot the optical window, angle the optical window, etc. The movement allows the direction of the light pathway 232 to be moved, allowing the light pathway 232 to be refocused for the purposes of identifying artifacts, going deeper into the volume, etc.

In one example, when a first, or initial light pathway 232 is provided and is focused on the middle of the target, a candidate irregularity may be viewed toward the perimeter of the field of view as a result of the initial light pathway 232. To verify the candidate irregularity is not merely an artifact, the steering assembly 263 steers the initial light pathway 232 to provide a second light pathway 232 that is focused on the area where the candidate irregularity has been identified. If the candidate irregularity is not detected when the light is focused on the identified location of the candidate irregularity, then an understanding is provided that the irregularity was as a result of an artifact, and not as the result of an irregularity.

Figure 3:
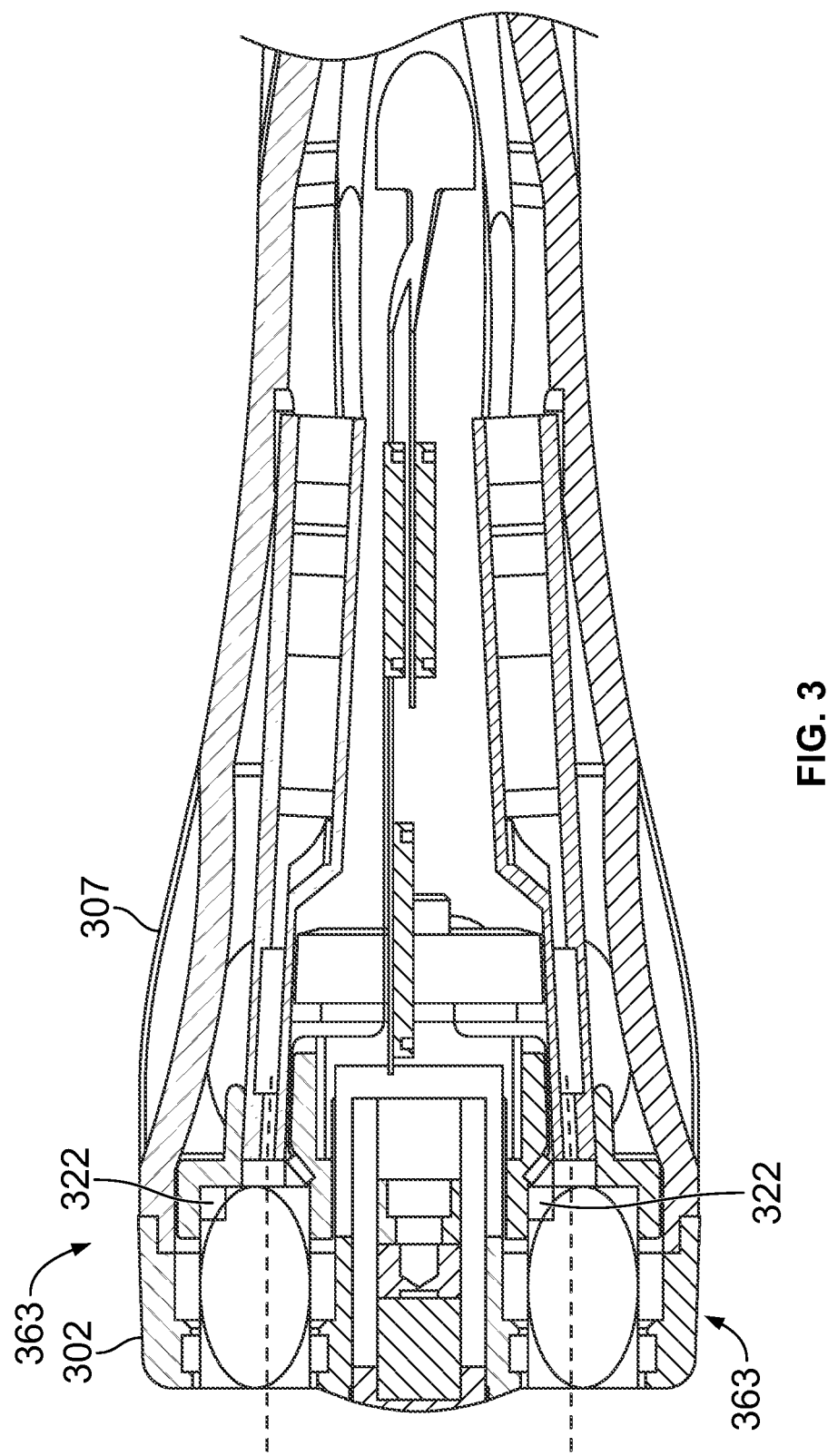
FIG. 3 shows a sectional view illustrating an embodiment of an optoacoustic system that may be used as a platform for the methods and devices disclosed herein.

FIG. 3 shows a cross-sectional view, respectively, of another embodiment of a probe 302 that in one example includes similar components as the probes 102 and 202 shown in FIGS. 1 and 2. In the embodiment of FIG. 3, the probe 302 comprises a housing 307 and instead of an optical window, the steering assembly 363 includes a deformable lens 320. The deformable lens 320 can be formed of an optical grade silicon that in one example can be generally rectangular that allows for turning or rotating. In another example, the steering assembly 363 includes a piston pump 322 is coupled to the deformable lens 320 such that the piston pump 322 can pump, or move hydraulic fluid into the lens. The hydraulic fluid functions to deform the lens by changing the radius of curvature of the lens. Consequently, the hydraulic fluid changes the radius of curvature of the deformable lens 320 to focus light on different locations and provide multiple movements of the deformable lens 320.

Figure 4:
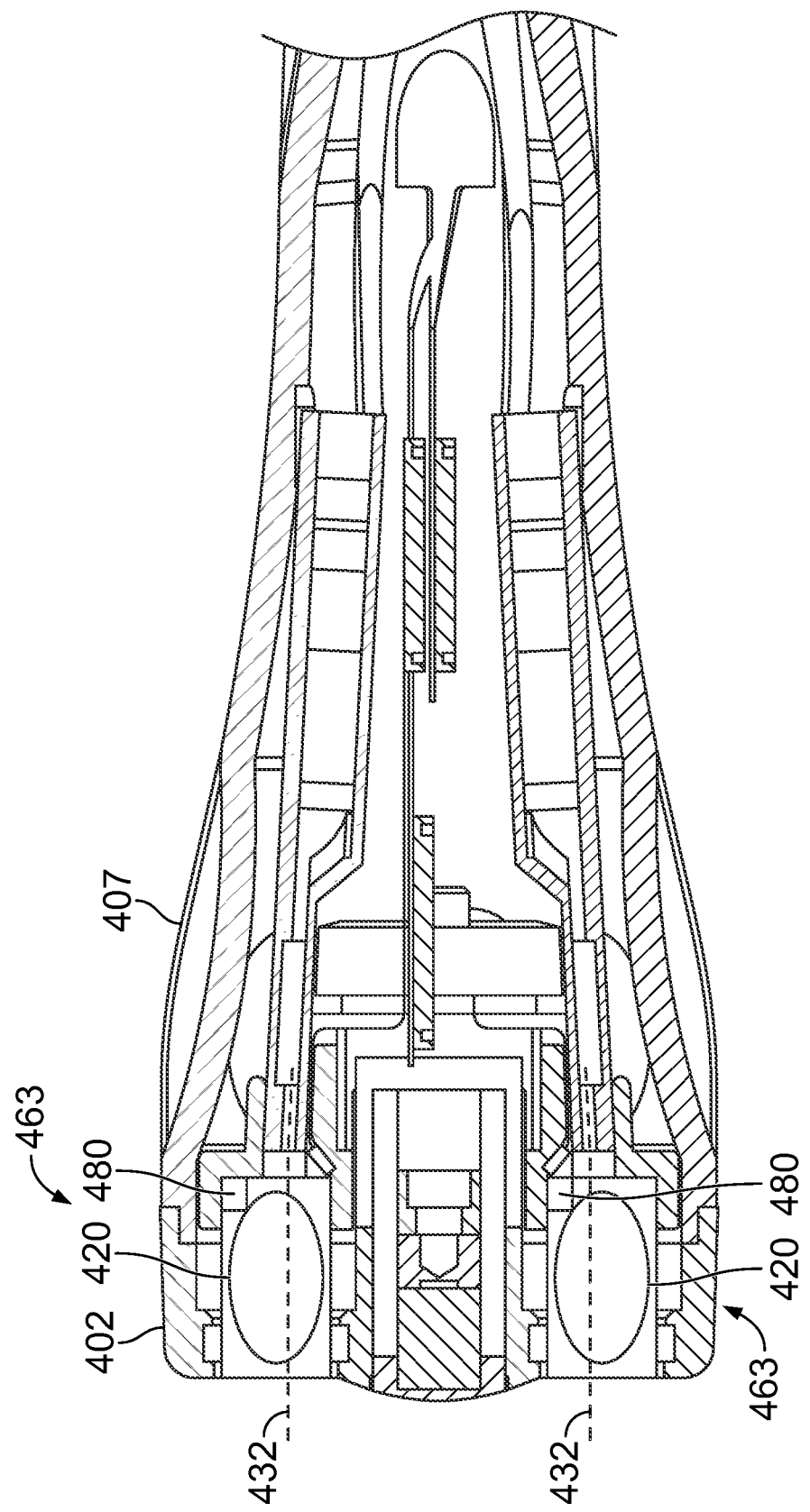
FIG. 4 shows a sectional view illustrating an embodiment of an optoacoustic system that may be used as a platform for the methods and devices disclosed herein.

FIG. 4 shows a cross-sectional view, respectively, of another embodiment of a probe 402 that in one example includes similar components as the probes 102 and 202 shown in FIGS. 1 and 2. In the embodiment of FIG. 4, the probe 402 comprises a housing 407, and includes a steering assembly 463 that instead of a deformable lens or optical window, utilizes a synthetic material 420. In particular, a synthetic fiber can be formed through polymerization by combining numerous monomers to form a long chain. These fibers may form an optical body 421 through which a light pathway 432 can pass. The optical body 421 can then be coupled to an actuator 480 of the steering assembly 463 to direct or steer the light path in a desired direction through movement, vibration, etc. of the optical body formed from the synthetic material.

Figure 5A:
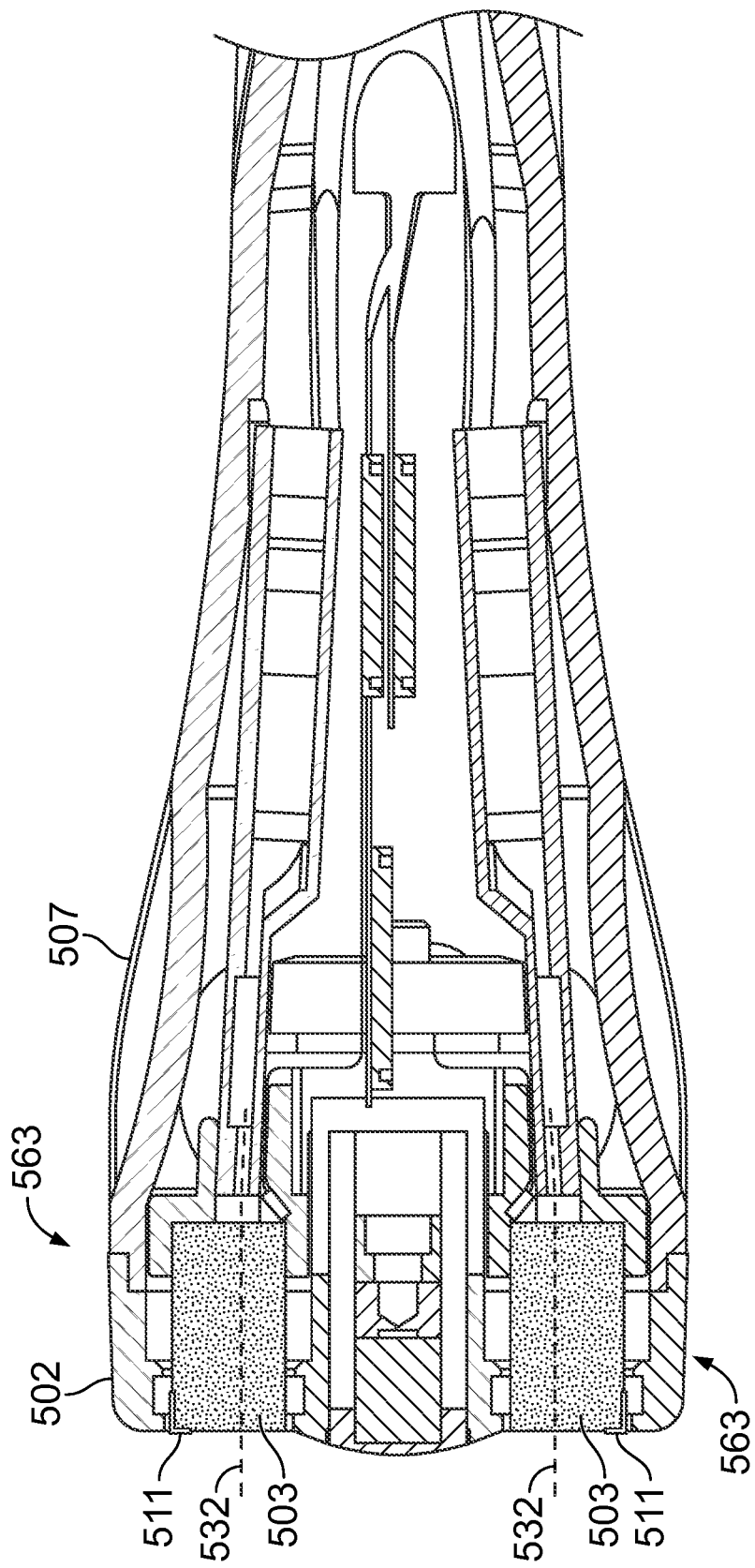
FIG. 5A shows a sectional view illustrating an embodiment of an optoacoustic system that may be used as a platform for the methods and devices disclosed herein.
Figure 5B:
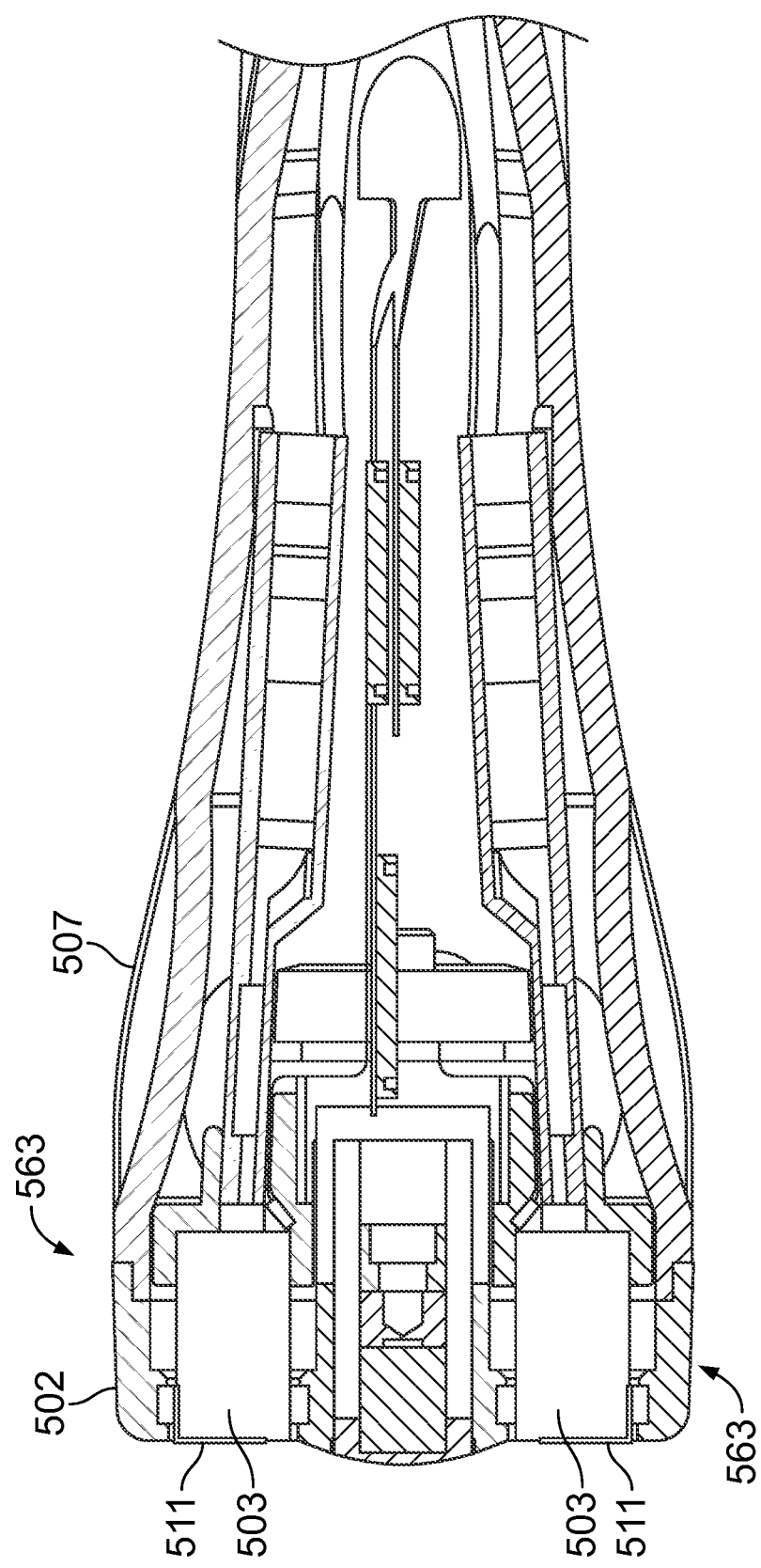
FIG. 5B shows a sectional view illustrating an embodiment of an optoacoustic system that may be used as a platform for the methods and devices disclosed herein.

FIGS. 5A and 5B show cross-sectional views, respectively, of another embodiment of a probe 502 that in one example includes similar components as the probes 102 and 202 shown in FIGS. 1 and 2. In the embodiment of FIGS. 5A and 5B, the probe 502 includes a housing 507 and has a steering assembly 563 that includes an optical window 503 utilized in association with a movable light absorbing material 511 that moves from a first position (FIG. 5A) to a second position (FIG. 5B). In one example, the light absorbing material is a black material. In example embodiments, the light absorbing material may be in the form of a shutter, sheet, solid material, cloth material, painted material, etc. In the first position, the light absorbing material does not block any portion of the optical window 503. As the light absorbing material moves from the first position to the second position, a portion of the light pathway 532 is blocked, resulting in only a portion of the light pathway 532 from exiting the optical window 503 onto the volume. In one example, in the second position, no light from the light pathway 532 exits the optical widow 503. In another example, the light absorbing material includes plural portions. In one example, a first portion is above the optical window and moves downwardly, a second portion is below the optical window and moves upwardly, a third portion is to one side of the optical window, and the fourth portion is to the opposite side of the optical window from the third portion. In this manner, light from the light pathway 532 may be focused on different locations of the volume depending on the movement of each of the first portion, second portion, third portion, and fourth portion of the light absorbing material 511.

Figure 6:
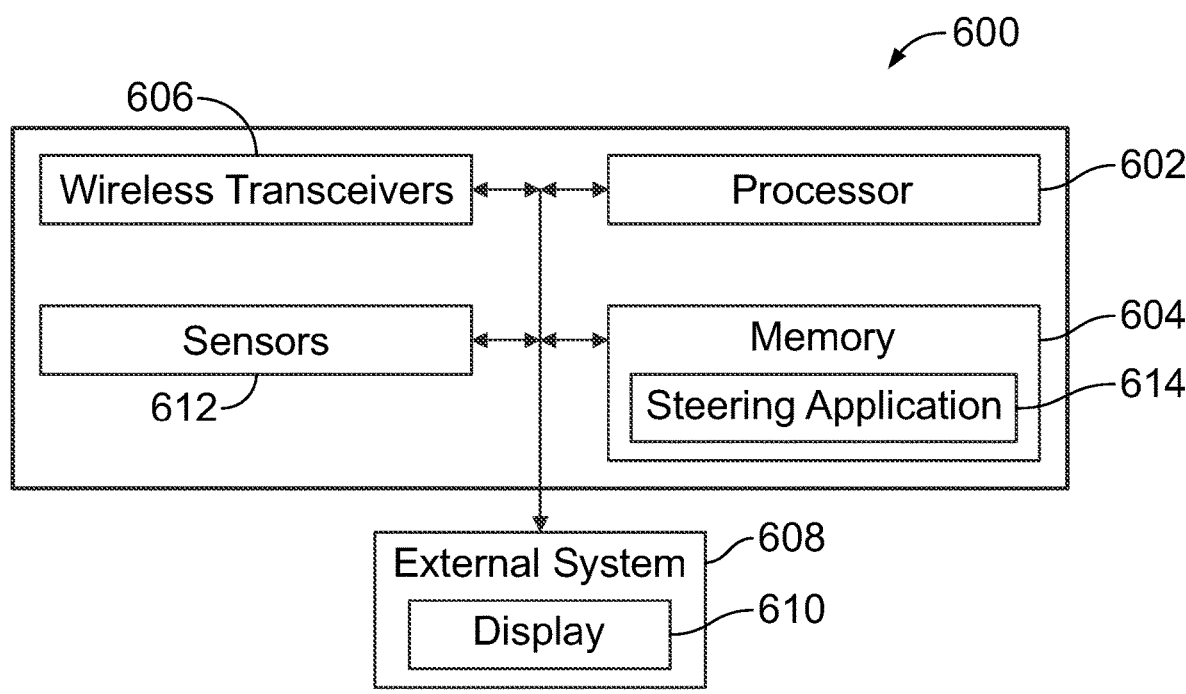
FIG. 6 shows a schematic block diagram illustrating an embodiment of microcontroller that may be used for the methods and devices disclosed herein.

FIG. 6 illustrates a schematic block diagram of a microcontroller 600. In one example, the microcontroller 600 is the computing subsystem 128 of FIG. 1. Alternatively, the microcontroller 600 is a component of the computing subsystem 128 of FIG. 1. The microcontroller can be utilized in any of the probes of FIGS. 1-5 to implement the method and processes described herein.

The microcontroller 600 includes one or more processors 602, and a memory 604 coupled to the one or more processors 602. The memory 604 stores instructions that can be executed by the one or more processors 602. The instructions may include instructions to perform processes and methods as described herein. The microcontroller 600 can also include a transceiver 606 for communicating with components and systems of the probe, along with external systems 608. The external systems 608 include imaging systems that have a display 610 in order to display images, including optoacoustic images, ultrasound images, or the like.

The microcontroller 600 also includes one or more sensors 612. The one or more sensors can include an ultrasound transducer, a feedback detector, or the like. In particular, the one or more sensors 612 in example embodiments can obtain a return signal generated as a result of a light pathway of a probe interacting with a volume to reflect the return signal to be detected by the sensor. The return signal in example embodiments can be light based, sound based, or the like.

In one example, stored within the memory 604 is a light pathway steering application 614. The light pathway steering application 614 includes instructions and in one example is configured to convert optoacoustic return signals into optoacoustic image data that can be provided on a display as an image, utilized as feedback for automatically steering the light pathway, etc. In one example, the steering application makes determinations related to irregularities and whether a candidate irregularity detected in a volume may be an artifact. In one example, based on the location of the irregularity in the volume compared to the scanning area of the volume, a determination can be made that the candidate irregularity may be an artifact. The steering application then determines the location of the candidate irregularity in the volume and steers the light pathway towards and on the candidate irregularity. The steering application 614 includes instructions to detect the return signals from where the candidate irregularity is determined to be located to determine if the candidate irregularity is an irregularity or an artifact. In another example, the steering application 614 can include instructions to obtain the skin density of a patient based on the return signals obtained, and determine whether the light pathway should be steered to facilitate penetration of the light of the light pathway through the skin of the patient. In example embodiments, the steering application 614 makes determinations by comparing a skin density determined to skin densities of other patients, by comparing a skin density determined to the historical data of skin densities related to the patient, by utilizing on a look-up table, algorithm, artificial intelligence algorithm, mathematical function, mathematical model, or the like. Still, based on the determination, the steering application provides instructions to automatically steer the light pathway, and continues to make determinations to increase the depth of penetration of the light of the light pathway through the volume. In one example, the steering application 614 provides instructions for an actuator, piston pump, other actuating device, etc. of a steering assembly to vary a light pathway.

Each probe in the embodiments of FIGS. 1-5, and the microcontroller of FIG. 6 provides a manner for steering the location of a light pathway without moving the probe. By steering the light pathway, when irregularities are detected, the light pathway can be steered to verify that the detected irregularity is not just an artifact due to reflection. In addition, by steering the light pathway, adjustments can be made on a patient by patient basis to navigate the light pathway through the skin and into a volume. In particular, skin is not uniform and can have varying densities. In one example, return signals obtained from an ultrasound transducer can by utilized as feedback, and one or more processors can automatically steer the light pathway according to the feedback. Alternatively, a feedback detector can be provided for detecting the density of the skin at the location where the light pathway is focused and the surrounding area. Based on the density, a determination can be made regarding whether a probability exists that steering of the light pathway will result in finding less dense skin, allowing for deeper penetration of the light.

In one example, a determined density is compared to an average skin density of a patient of the same sex, skin pigmentation, age, etc. In another example, the skin density of the patient is measured for each scan and a comparison is done to the skin density of the patient during a previous scan. In yet another example, the light pathway is automatically steered along the patient's skin and densities are continuously calculated, or determined in a scanning area. After the scan is complete, one or more processors can determine the location of least density for the scanning area and steer the light pathway to that location for imaging. In each example, measurements and determinations are made to determine the skin density of the volume at the scanning area, and modify the location of the light pathway within the scanning area based on the feedback. As a result, by using the ultrasound feedback, the light pathway may be tuned, or adjusted to accommodate different skin densities. In one example, a physician steers the light pathway based on the determined skin densities, whereas alternatively, the one or more processors may automatically steer the light pathway based on the determined skin densities.

Figure 7:
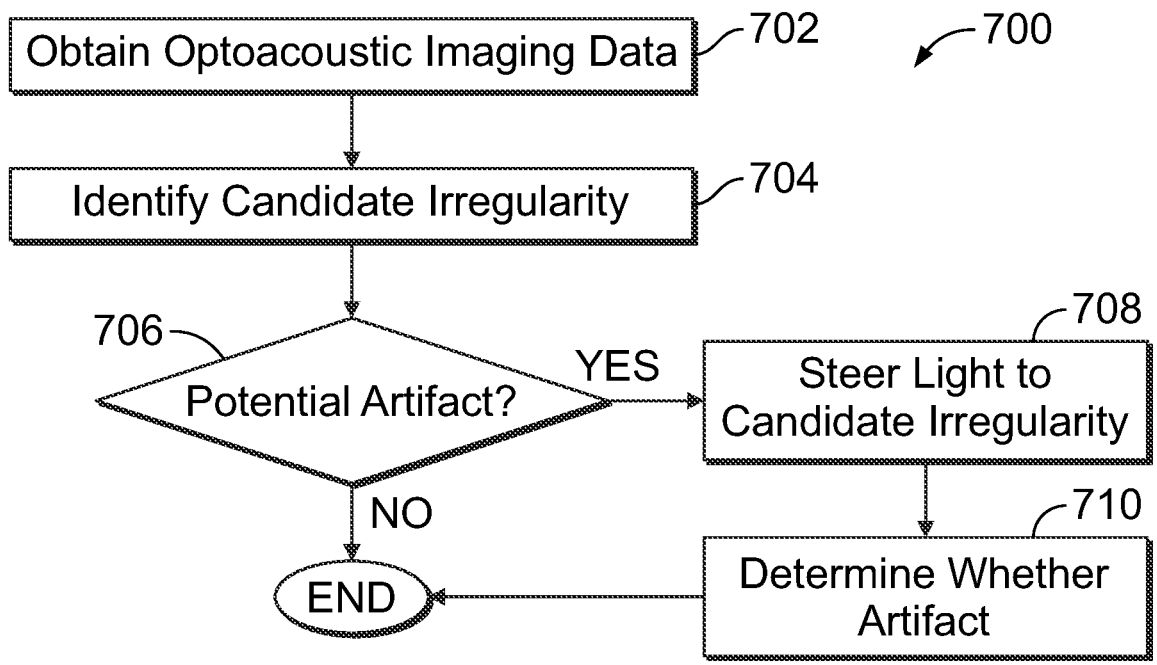
FIG. 7 shows a schematic block diagram illustrating a process for optoacoustic imaging for embodiment disclosed herein.

FIG. 7 illustrates a block diagram of a process 700 for optoacoustic imaging with an optoacoustic probe. Any of the example optoacoustic probes of FIGS. 1-5, and the microprocessor of FIG. 6 can be utilized to implement the process. In particular, the process is based on a probe that includes a light pathway that can be steered when the probe is push against and engaging the volume. By steering the light pathway, determinations related to artifacts, skin density, etc. may be determined, improving imaging techniques of a physician.

At 702, a probe directs a light pathway to a location in a scanning area of a volume to obtain optoacoustic imaging data. The scanning area can be any portion of the volume that can be reached by the light pathway as a result steering of at least one light source that generates light for the light pathway. In one example, the scanning area includes the breast of a patient. In another example embodiment, the scanning area includes the prostrate of a patient. In one example, the ultrasound imaging data can be utilized for optoacoustic imaging of the volume in order to detect irregularities in the volume.

At 704, the probe identifies a candidate irregularity in the scanning area. The candidate irregularity may be an irregularity such as a lump, masses, mass of cells, tumor, etc. within the volume, or a false reading including a false reading caused as a result of a light artifact. By directing the light pathway through the volume, return signals reflect off of the volume, including irregularities in the volume into the probe. The reflected return signals can then be detected by a transducer, feedback detector, etc. Still, on occasion the return signal can be reflected off of walls of the probe, the window, etc. (e.g. a light artifact) that results in an identification of an irregularity in the volume when an irregularity is not actually in the volume.

At 706 optionally, one or more processors determine whether the candidate irregularity may be an artifact. In particular, based on the location, return signal strength, etc. of a return signal obtained to determine a candidate irregularity is detected may increase a probability that the candidate irregularity is an artifact. As an example, when the candidate irregularity is aligned with the light pathway, are greater probability exists that the candidate irregularity is an irregularity than if the candidate irregularity is not aligned with the light pathway. To this end, a threshold distance from alignment can be provided, such as 1 mm, where any irregularity within the 1 mm threshold is considered not an artifact. Alternatively, if the candidate irregularity is more than the threshold distance from the light pathway, a probably exists that the irregularity is an artifact. In another embodiment, the strength of the return signal obtained may be utilized to determine if the candidate irregularity is an artifact. Because artifacts are reflected return signals, they often are weaker return signals than when coming from an irregularity. Optionally, a threshold return signal strength is provided such that any candidate signal detected above the threshold is considered an irregularity, while any return signal detected below the signal may be an artifact.

If at 706 a determination is made that the candidate irregularity is not an artifact, the process ends. If at 706 a determination is made that the candidate irregularity may be an artifact, then at 708 the one or more processors steer the light pathway toward the location of the candidate irregularity. Based on the detected return signals, the one or more processors can determine the location of the candidate irregularity. The determination can be made utilizing a calculation, algorithm, comparison of historical data, mathematical formula, mathematical model, etc. Consequently, the light pathway may be steered to the location where the candidate irregularity is located.

At 710 a determination is made whether the candidate irregularity is an artifact. By steering the light pathway directly at the determined location of the candidate irregularity, if the candidate irregularity is an irregularity, the light pathway will alight with the irregularity, the return signal becomes stronger, etc. confirming that an irregularity is detected. Alternatively, if the irregularity is merely an artifact, no irregularity is detected because the light pathway has moved, resulting in the reflected return signal causing the artifact originally to no longer be provided. As a result a determination can be made that the candidate irregularity is an artifact without the need of addition testing or analysis.

Figure 8:
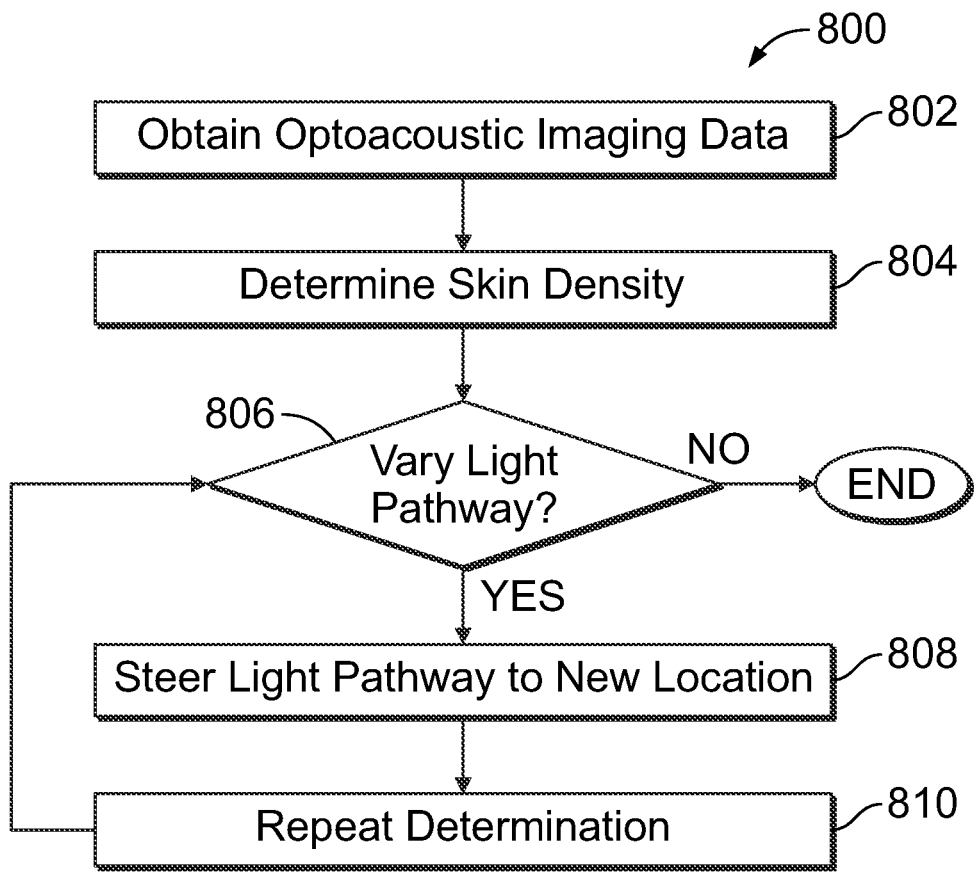
FIG. 8 shows a schematic block diagram illustrating a process for optoacoustic imaging for embodiment disclosed herein.

FIG. 8 illustrates a block diagram of a process 800 for optoacoustic imaging with an optoacoustic probe. Similar to FIG. 7, in one example, any optoacoustic probe of FIGS. 1-5 or the microcontroller of FIG. 6 are utilized to implement the process. In particular, the process is provided to navigate through differing skin densities.

At 802, a probe directs a light pathway to a location in a scanning area to obtain ultrasound imaging data by detecting return signals reflected off the volume. As with the process of FIG. 7, the scanning area can be any portion of the volume that can be reached by the light pathway as a result steering of at least one light source that generates light for the light pathway. In one example, the ultrasound imaging data can be utilized to detect irregularities in the volume. In one example, a transducer obtains the return signals. Alternatively, an auxiliary, or feedback detector obtains the return signals.

At, 804, one or more processors determine the skin density at the location in the scanning area. In one example, the one or more processors use an algorithm, look-up table, mathematical formula, mathematical model, etc. to determine the skin density at the location based on the return signals obtained.

At 806, one or more processors make a determination regarding whether the light pathway should be varied. The determination can be made utilizing a look-up table, comparison to historical data, algorithm, mathematical model, artificial intelligence algorithm, or the like. In one example, a threshold density is provided such that any densities determined that are less than the threshold indicates that the light pathway should not be varied, whereas any densities that are determined to be greater than the threshold density indicates that the light pathway should be varied.

If at 808, the one or more processors determine that the light pathway should not be varied, and the process ends. In particular, if the density of the skin of the patient allows for deep penetration into the volume, steering of the light pathway does not occur. However, if the one or more processors determine that the light pathway should be varied, at 810 the one or more processors steer the light pathway to a new location on the volume. In one example, to steer the light the optical window is rotated by a motor. In another example to steer the light a deformable lens is provided that is hydraulically controlled. In yet another example, a synthetic material with synthetic fiber is utilized to vary the light. In one embodiment, a light absorbing material that moves from a first position to a second position along the optical window is provided. Alternatively, an SLM is utilized to vary and control the location of the light pathway by varying the phase of a light source.

At 812 the one or more processors repeat the determination step and continue to vary the light pathway until a pathway through the volume with a desired density is obtained. As a result, the light pathway is able to penetrate deeper into the volume to find irregularities.

The present system and methods are described above with reference to block diagrams and operational illustrations of methods and devices comprising an optoacoustic probe. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, FPGA, or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used in this description and in the following claims, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" unless the content clearly dictates otherwise.

The recitation herein of numerical ranges by endpoints includes all numbers subsumed within that range (e.g. 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

Those skilled in the art will recognize that the methods and systems of the present disclosure may be implemented in many manners and as such are not to be limited by the foregoing example embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces, and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. An optoacoustic probe for optoacoustic imaging of a volume, comprising:
    a housing extending from a distal end operable to contact the volume to a proximal end;
    a light source within the housing and configured to generate light that is transmitted along a light pathway to generate return signals when the light reacts with the volume;
    a transducer assembly including a transducer configured to receive the optoacoustic return signals and an acoustic lens provided over the transducer;
    a steering assembly coupled within the housing at the distal end of the housing and configured to steer the light pathway to generate the light along the light pathway at different scanning areas of the volume, the volume located outside of the housing of the probe;
    a microcontroller including one or more processors, and a memory coupled to the one or more processors, wherein the memory stores program instructions, wherein the program instructions are executable by the one or more processors to:
        obtain the return signals generated from the light pathway reflecting from the volume; and
        steer the light pathway with the steering assembly based on the return signals.

2. The optoacoustic probe of claim 1, wherein the steering assembly comprises a spatial light modulator (SLM) coupled to the light source and configured to deflect the light pathway.

3. The optoacoustic probe of claim 2, wherein the SLM is a phase only one-dimensional phase modulator formed of a liquid crystal material.

4. The optoacoustic probe of claim 1, wherein the steering assembly comprises:
    an optical window configured to transmit the light along the light pathway to the volume; and
    an actuator coupled to the optical window to move the optical window from a first angle to a second angle.

5. The optoacoustic probe of claim 4, wherein the optical window is cylindrical, and the actuator is configured to rotate the optical window from a first position to a second position to steer the light pathway.

6. The optoacoustic probe of claim 1, wherein the steering assembly comprises a deformable lens having a radius of curvature configured to vary to steer the light pathway.

7. The optoacoustic probe of claim 6, wherein the steering assembly further comprises a piston pump coupled to the deformable lens to vary hydraulic fluid within the deformable lens to vary the radius of curvature.

8. The optoacoustic probe of claim 1, wherein the steering assembly comprises a synthetic material coupled to an actuator to steer the light pathway.

9. The optoacoustic probe of claim 1, wherein the one or more processors of the microcontroller are further configured to:
- identify a portion of a candidate irregularity based on the return signals;
- determine a location of the candidate irregularity; and
- steer the light pathway toward the candidate irregularity based on determining the location of the candidate irregularity.

10. The optoacoustic probe of claim 9, wherein the one or more processors of the microcontroller are further configured to:
- verify that the candidate irregularity is not an artifact based on steering the light pathway toward the candidate irregularity.

11. The optoacoustic probe of claim 1, wherein the one or more processors of the microcontroller are further configured to:
- determine skin density of a patient based on the return signals;
- steer the light pathway based on the skin density determined.

12. The optoacoustic probe of claim 1, wherein the steering assembly comprises:
- an optical window disposed at the distal end of the housing that is configured to transmit the light along the light pathway to the volume.

\* \* \* \* \*